United States Patent
Leopold et al.

(10) Patent No.: US 7,901,448 B2
(45) Date of Patent: Mar. 8, 2011

(54) VASCULAR PROTHESIS HAVING INTERDIGITATING EDGES AND METHODS OF USE

(75) Inventors: Eric Leopold, Redwood City, CA (US); Tim Huynh, Milpitas, CA (US)

(73) Assignee: NovoStent Corporation, Mountian View, CA (US)

( * ) Notice: Subject to any disclaimer, the term of this patent is extended or adjusted under 35 U.S.C. 154(b) by 0 days.

(21) Appl. No.: 11/241,341

(22) Filed: Sep. 30, 2005

(65) Prior Publication Data

US 2006/0052861 A1 Mar. 9, 2006

(51) Int. Cl.
 *A61F 2/06* (2006.01)
 *A61M 29/00* (2006.01)

(52) U.S. Cl. ........................................ 623/1.15; 606/108

(58) Field of Classification Search .................. 623/1.15, 623/1.11, 1.12, 1.13, 1.14, 1.16, 1.17, 1.18, 623/1.19; 606/198, 195, 194, 108, 191
See application file for complete search history.

(56) References Cited

U.S. PATENT DOCUMENTS

| | | | |
|---|---|---|---|
| 5,575,816 A | 11/1996 | Rudnick et al. | |
| 5,707,387 A | 1/1998 | Wijay | |
| 5,824,053 A * | 10/1998 | Khosravi et al. | 623/1.15 |
| 5,833,699 A | 11/1998 | Chuter | |
| 5,897,588 A | 4/1999 | Hull et al. | |
| 5,906,639 A | 5/1999 | Rudnick et al. | |
| 5,968,091 A * | 10/1999 | Pinchuk et al. | 623/1.16 |
| 6,165,210 A | 12/2000 | Lau et al. | |
| 6,171,334 B1 | 1/2001 | Cox | |
| 6,190,403 B1 | 2/2001 | Fischell et al. | |
| 6,315,708 B1 | 11/2001 | Salmon | |
| 6,319,277 B1 | 11/2001 | Rudnick et al. | |
| 6,340,366 B2 | 1/2002 | Wijay | |
| 6,352,561 B1 * | 3/2002 | Leopold et al. | 623/1.23 |
| 6,425,915 B1 | 7/2002 | Khosravi | |
| 6,508,834 B1 * | 1/2003 | Pinchasik et al. | 623/1.16 |
| 6,660,032 B2 | 12/2003 | Klumb et al. | |
| 6,736,844 B1 * | 5/2004 | Glatt et al. | 623/1.22 |
| 6,821,292 B2 | 11/2004 | Pazienza et al. | |
| 6,949,121 B1 * | 9/2005 | Laguna | 623/1.35 |
| 7,169,175 B2 * | 1/2007 | Cottone et al. | 623/1.22 |
| 2001/0047199 A1 | 11/2001 | Wijay | |
| 2002/0040238 A1 | 4/2002 | Rudnick et al. | |
| 2003/0093142 A1 * | 5/2003 | Edelman et al. | 623/1.15 |
| 2004/0186556 A1 | 9/2004 | Hogendijk et al. | |
| 2004/0193251 A1 | 9/2004 | Rudnick et al. | |

FOREIGN PATENT DOCUMENTS

WO 2007/041586 4/2007

OTHER PUBLICATIONS

Office Action Mailed Jun. 26, 2008 for U.S. Appl. No. 10/746,668, filed Dec. 23, 2003. Amendment/Request Reconsideration After Non-Final Rejection filed on Sep. 25, 2008 for U.S. Appl. No. 10/746,668, filed Dec. 23, 2003.

* cited by examiner

*Primary Examiner* — Vy Q Bui

(74) *Attorney, Agent, or Firm* — James E. Hann; Haynes Beffel & Wolfeld LLP

(57) ABSTRACT

The present invention is directed to an implantable vascular prosthesis configured for use in a wide range of applications, such as treating aneurysms, maintaining patency in a vessel, and providing controlled delivery of therapeutic agents to a vessel wall. The prosthesis comprises a helical body having a plurality of turns, wherein the proximal and distal edges of the turns of the prosthesis has a pattern that interdigitates when the prosthesis assumes the deployed configuration. The prosthesis optionally may comprise a radially expanding distal portion coupled to the helical body for facilitating placement of the prosthesis within a body vessel.

9 Claims, 3 Drawing Sheets

VASCULAR PROTHESIS HAVING INTERDIGITATING EDGES AND METHODS OF USE

REFERENCE TO RELATED APPLICATIONS

This application is related to U.S. patent application Ser. No. 10/342,427, filed Jan. 13, 2003.

FIELD OF THE INVENTION

The present invention relates to an implantable vascular prosthesis having a helical body comprising a plurality of turns with edges that interdigitate in the deployed state.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath, then self-expand when the sheath is retracted. Such stents have several drawbacks, for example, the stents may experience large length changes during expansion and may shift within the vessel prior to engaging the vessel wall, resulting in improper placement. Additionally, many self-expanding stents have relatively large delivery profiles because the configuration of their struts limit compression of the stent. Accordingly, such stents may not be suitable for use in smaller vessels, such as cerebral vessels and coronary arteries.

Other drawbacks associated with the use of coils or stents in the treatment of aneurysms is that the coils or stents, when deployed, may have a tendency to remodel or straighten a delicate cerebral vessel, which may cause further adverse consequences. Moreover, such devices may not adequately reduce blood flow from the cerebral vessel into the sac of the aneurysm, which may increase the likelihood of rupture. Generally, if a greater surface area is employed to cover the sac, the delivery profile of the device may be compromised due to the increased surface area, and the device also may be more rigid and cause remodeling of the vessel.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, then constrained within a delivery sheath. The delivery sheath is retracted to expose the distal portion of the stent and anchor the distal end of the stent. As the delivery sheath is further retracted, the subsequent individual turns of the stent unwind to conform to the diameter of the vessel wall.

The stent described in the foregoing publication has several drawbacks. For example, due to friction between the turns and the sheath, the individual turns of the stent may bunch up, or overlap with one another, when the delivery sheath is retracted. In addition, once the sheath is fully retracted, the turns may shift within the vessel prior to engaging the vessel wall, resulting in improper placement. Moreover, because the distal portion of the stent may provide insufficient engagement with the vessel wall during subsequent retraction of the remainder of the sheath, ambiguity concerning accuracy of the stent placement may arise.

When utilizing stents in interventional procedures, it may be advantageous to deliver therapeutic agents to a vessel wall via the surface of the stent. Such drug eluting stents have many advantages, such as controlled delivery of therapeutic agents over an extended period of time without the need for intervention, and reduced rates of restenosis after angioplasty procedures. Typically, the drug is disposed in the matrix of bioabsorbable polymer coated on an exterior surface of the struts of the stent. The drug gradually elutes from the polymer or is released into a vessel wall as the polymer biodegrades. The quantity of the therapeutic agent provided by the stent generally is limited by the surface area of the struts. Increasing the surface area of the struts may enhance drug delivery capability, but may compromise the overall delivery profile of the stent. Accordingly, there exists a need for a prosthesis having a reduced delivery profile and enhanced drug delivery capabilities.

Helically wound, such as described in U.S. Pat. No. 4,503,569 to Dotter, lack a controllable degree of surface area. For example, the stent is only in contact with a narrow portion of the bodily vessel and offers limited support for the tissue between adjacent turns or winds. Moreover, adjacent turns may move relative to each other, resulting in larger gaps between some turns as compared to others. Still further, radial compressive forces may become concentrated on only a few turns of the stent, rather than being distributed over a longer length of the stent surface.

Other helical stent designs have attempted to overcome this problem by increasing the width of the contact area. For example, the width of the helical body of the stent may be widened so as to resemble a ribbon, such as disclosed in U.S. Pat. No. 5,833,699 to Chuter. Nevertheless, such designs still may not adequately distribute radial compressive forces to adjacent turns of the stent. Also, because the space between adjacent turns may vary according to the inner diameter of the bodily vessel, the extent of any such force distribution may be variable.

In view of these drawbacks of previously known devices, it would be desirable to provide apparatus and methods for an implantable vascular prosthesis that may be configured for use in a wide range of applications including, but not limited to, treating aneurysms, maintaining patency in a vessel, and delivering drugs to a vessel wall.

It also would be desirable to provide apparatus and methods for a vascular prosthesis that is flexible enough to conform to a natural shape of a vessel without substantially remodeling the vessel.

It further would be desirable to provide apparatus and methods for a vascular prosthesis that facilitates controlled deployment of the prosthesis at a desired location within a vessel.

It still further would be desirable to provide apparatus and methods for a vascular prosthesis that has a selectable surface area to facilitate in-vivo delivery of therapeutic agents.

It yet further would be desirable to provide apparatus and methods for a helical vascular prosthesis that reduces the area of unsupported tissue between adjacent turns.

It also would be desirable to provide apparatus and methods for a helical vascular prosthesis that enhances distribution of compressive forces over multiple adjacent turns.

SUMMARY OF THE INVENTION

In view of the foregoing, it is an object of the present invention to provide apparatus and methods for an implantable vascular prosthesis that may be configured for use in a wide range of applications including, but not limited to, treating aneurysms, maintaining patency in a vessel, and delivering drugs to a vessel wall.

It is also an object of this invention to provide apparatus and methods for a vascular prosthesis that is flexible enough to conform to a natural shape of a vessel without substantially remodeling the vessel.

It is a further object of the present invention to provide apparatus and methods for a vascular prosthesis that facilitates controlled deployment of the prosthesis at a desired location within a vessel.

It is another object of this invention to provide apparatus and methods for a vascular prosthesis that has a selectable surface area to facilitate in-vivo delivery of therapeutic agents.

It is a further object of the present invention to provide apparatus and methods for a helical vascular prosthesis that reduces the area of unsupported tissue between adjacent turns.

It is a still further object of this invention to provide apparatus and methods for a helical vascular prosthesis that enhances distribution of compressive forces over multiple adjacent turns.

These and other objects of the present invention are accomplished by providing a vascular prosthesis having a contracted state and a deployed state configured to engage a vessel wall and adapt to a natural curvature of the vessel wall. In a preferred embodiment, the vascular prosthesis comprises a shape memory material, such as Nitinol, forming a helical mesh body comprising a plurality of turns. The turns of the helical section have proximal and distal edges that interdigitate when deployed within a body vessel, thereby improving coverage and support of the vessel wall, and enhancing the distribution of compressive forces over adjacent turns of the helical mesh section.

In accordance with the principles of the present invention, the edges of the helical mesh section may have any of a number of shapes that permit interdigitation, such as sinusoidal, zig-zag or other non-straight configuration that facilitates interdigitation in the deployed state. In a preferred embodiment, the edges of the helical section have a sinusoidal shape comprising a series of crests and troughs configured so that, in the deployed state, the crests of the edge on one turn are disposed beside the troughs of the edge on the adjacent turn. Such interdigitation permits adjacent turns to reside in close proximity to one another, improves the uniformity of gaps between the turns, and serves to diffuse compressive loads over multiple adjacent turns of the helical section.

In accordance one preferred embodiment, an optional radially self-expanding distal anchoring section is coupled to distal end of the helical mesh portion. The anchoring section is delivered within a target vessel in a contracted state, constrained within an outer sheath due to the radially inward compressive forces applied by the sheath. The helical mesh section is provided in the contracted state when the plurality of turns of the helical mesh are wound down to a smaller configuration, wherein adjacent turns preferably at least partially overlap, and then are constrained within the outer sheath.

In a preferred method of operation, the proximal helical mesh and distal anchoring sections are provided in their respective contracted states within the outer sheath and the prosthesis is fluoroscopically advanced into a selected vessel using techniques that are per se known in the art. The proximal section then is positioned adjacent a target region of a vessel, such as an aneurysm or a stenosed region. At this time, the distal section is positioned distal of the target region. The outer sheath then is retracted proximally to cause the distal section to self-deploy and engage an inner wall of the vessel distal of the target region.

Once the distal section is securely anchored distal of the target region, the outer sheath further is retracted to cause the helical proximal section to self-deploy and engage the vessel wall. Advantageously, the distal anchoring element permits the turns of the helical mesh section to unwind in a controlled manner as the outer sheath is retracted so that the edges of the helical section interdigitate. In alternative embodiments, the distal anchor may be omitted, so that the vascular prosthesis comprises only the helical mesh body.

In accordance with another aspect of the present invention, the plurality of turns of the helical mesh section comprise a substantially increased surface area relative to conventional stents that have a plurality of interconnected struts. The increased surface area of the turns is particularly advantageous for localized drug delivery. The turns may be coated with a drug-laden polymer coating or, alternatively, one or more dimples or through holes may be disposed in a lateral surface of the turns to elute drugs over an extended period of time.

The vascular prosthesis may be used in a wide range of applications, such as treating aneurysms, maintaining patency in a vessel, e.g., after an angioplasty procedure, and other procedures requiring a controlled delivery of therapeutic drugs to a vessel wall.

Methods of using the vascular prosthesis of the present invention, for example, in the treatment of an aneurysm, also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an implantable vascular prosthesis configured for use in a wide range of applications, such as treating aneurysms, maintaining patency in a vessel, and allowing for the controlled delivery of therapeutic agents to a vessel wall. The prosthesis has a substantially small delivery profile compared to other known devices, while having an increased surface area to allow for delivery of the therapeutic agents. Additionally, the prosthesis is configured to conform to a vessel wall without substantially remodeling the vessel, and further is configured to provide improved deployment accuracy during deployment relative to previously known devices.

Figure 1A:
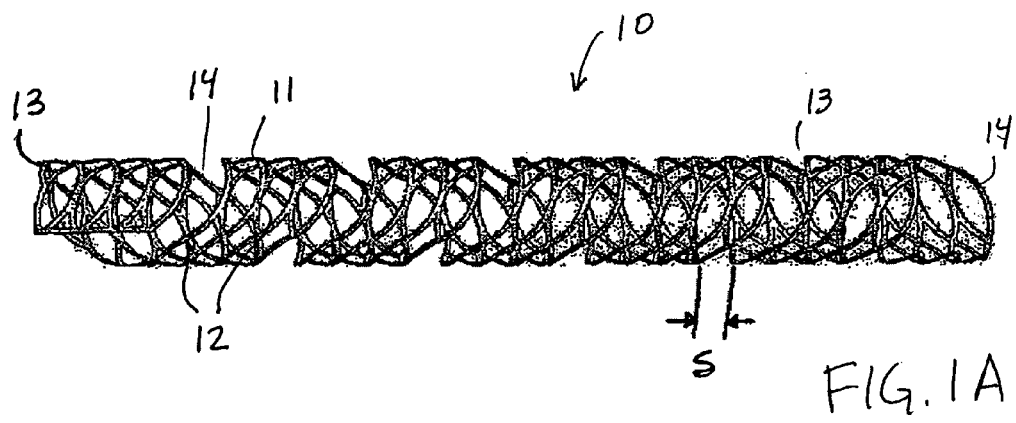
FIGS. 1A-1B are, respectively, a side view and a plan view, unrolled, of a vascular prosthesis of the present invention.
Figure 1B:
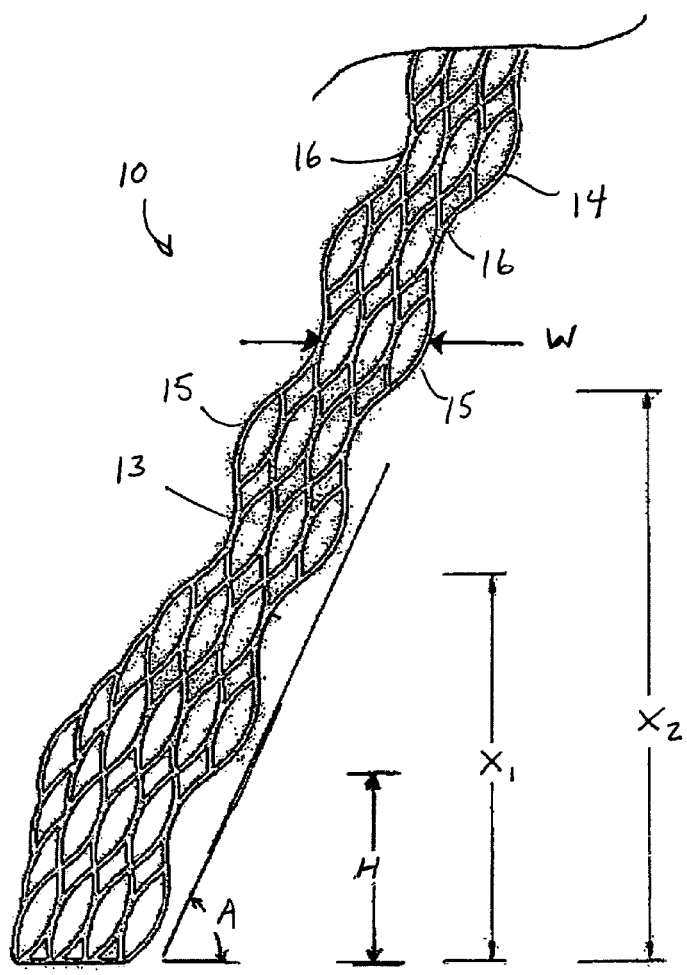

Referring now to FIGS. 1A and 1B, a first embodiment of a vascular prosthesis constructed in accordance with principles of the present invention is described. Vascular prosthesis 10 comprises helical mesh body 11 having a plurality of turns capable of transitioning between a wound down contracted state and an expanded deployed state. Mesh body 11 comprises a plurality of cells 12 that are aligned along the helical axis of the prosthesis. Each cell comprises a plurality of struts that define openings, which may vary in shape or size.

In FIG. 1B, prosthesis 10 is shown unrolled and flattened, so that distal edge 13 and proximal edge 14 are more clearly visible. In accordance with the principles of the present invention, each of distal edge 13 and proximal edge 14 defines a series of crests 15 and troughs 16. When prosthesis 10 is deployed, crests 15 on proximal edge 14 are immediately adjacent to troughs 16 on distal edge 13. Likewise, troughs 16 on proximal edge 14 are immediately adjacent to crests 15 of distal edge 13.

Vascular prosthesis 10 preferably is made from a solid tubular member comprising a shape memory material, such a nickel-titanium alloy (commonly known in the art as Nitinol). The solid tubular member is laser cut, using techniques that are per se known in the art, to a desired deployed configuration, as depicted in FIG. 1A. An appropriate heat treatment, also known in the art, then may be applied to vascular prosthesis 10 while the device is held in the desired deployed configuration. The treatment of the shape memory material allows vascular prosthesis 10 to self-deploy to the desired deployed configuration from the contracted delivery configuration.

In some embodiments, prosthesis 10 also may comprise a polymer coating capable of eluting drugs or bioactive agents, or a biodegradable coating that releases an active agent, such as a drug, into the blood stream or vessel wall. As a further alternative, prosthesis 10 may itself comprises a polymer or biodegradable polymer.

Still referring to FIG. 1B, distal edge 13 and proximal edge 14 have wavelike patterns that are 180 degrees out of phase across width W of the turn. Accordingly, when prosthesis 10 is in the deployed configuration, distal edge 13 and proximal edge 14 are located in close proximity to one another. This arrangement reduces space S between adjacent turns of the prosthesis, and facilitates distribution of compressive forces applied to the prosthesis.

Still referring to FIG. 1B, a relationship between the desired circumference of vascular prosthesis 10 and the pattern along an edge, for example proximal edge 14, is described. Wave height H can be related to the number n of waves in each turn of the prosthesis using the equation $H=(\pi)(ID)/n$. Thus, in FIG. 1B, vascular prosthesis 10 having two waves, or two series of repeating patterns, per turn, would correspond to a body vessel having an inner circumference of X1. Likewise, vascular prosthesis 50 having three waves, or three series of repeating patterns, per turn, corresponds to a body vessel having an inner circumference of X2. Accordingly, the inner circumference of the vessel (or outer of the prosthesis) may be found by multiplying the inner diameter ID by pi ($\pi$). It should be understood that angle A or width W of helical mesh body 11 also may be adjusted so that crests 15 of one turn align with troughs 16 of an adjacent turn.

In some embodiments, the patterns formed by distal edge 13 and proximal edge 14 are periodic, such as a sinusoid, a series of triangular protrusions and depressions, or other series. Alternatively, the pattern may increase in size from a proximal turn to a distal turn of the prosthesis, e.g., a series of triangular protrusions and depressions. Preferably, vascular prosthesis 10 has an edge having at least one crest 15 extending toward the adjacent turn, and another edge having at least one trough 16 of complementary shape.

As will be apparent to one skilled in the art, the configuration of helical mesh body 11 of FIG. 1 is intended to be merely illustrative. Other combinations of struts and openings may be employed. As will be apparent to those skilled in the art, the combination of struts and openings may be selected along the length of helical mesh body 11, for example, to selectively increase surface area and drug delivery capabilities or to influence flow dynamics within a vessel.

Figure 2A:
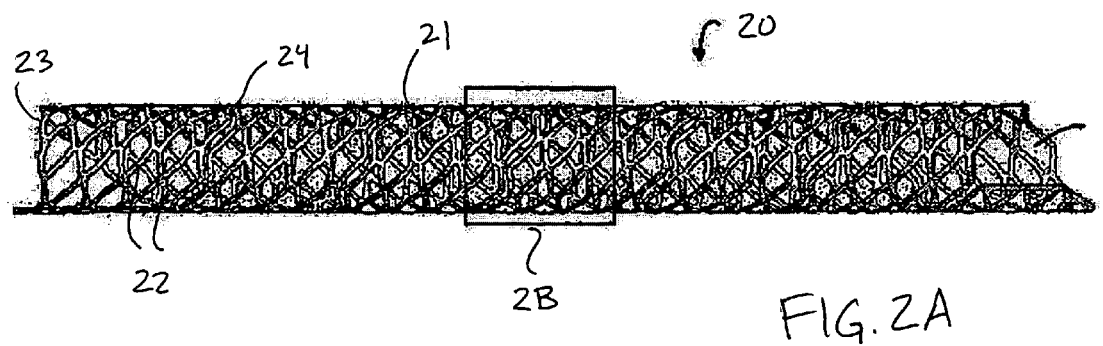
FIGS. 2A and 2B are, respectively, a side view and detailed view of an alternative embodiment of a prosthesis of the present invention.
Figure 2B:
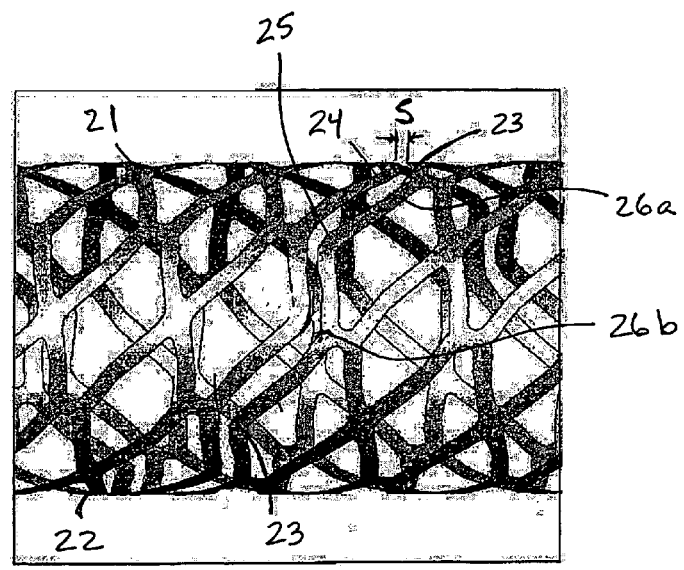

Referring now to FIGS. 2A and 2B, an alternative embodiment of a vascular prosthesis constructed in accordance with the present invention is described. Vascular prosthesis 20 is similar is design to prosthesis 10 of FIG. 1, and includes helical mesh body 21 formed from cells 22 and having a plurality of turns. Cells 22 comprise a plurality of interconnected struts that define substantially diamond-shaped openings. It of course should be understood that the struts comprising cells 22 may have numerous other shapes (e.g., triangular, rhomboidal, pentagonal, etc.) without departing from the scope of the present invention, as discussed above.

Helical mesh body 20 includes distal edge 23 and proximal edge 24. The diamond-shaped design of cells 22 produces a series of triangular-shaped crests 25 and troughs 26 along each of distal edge 23 and proximal edge 24. As depicted in FIG. 2B, the crests and troughs of the distal and proximal edges interdigitate when the stent expands to its deployed configuration. In particular, crest 25 is disposed more proximal than either of neighboring troughs 26a and 26b.

The foregoing configuration provides for some redistribution of compressive loads between adjacent turns, and in addition, allows proximal edge 24 to limit the motion of distal edge 23 on the adjacent turn. Because space S between adjacent turns is on the order of the width of the opening in cells 22, this configuration also is expected to better prevent tissue prolapse into space S compared to previously known helical stent designs.

Figure 3:
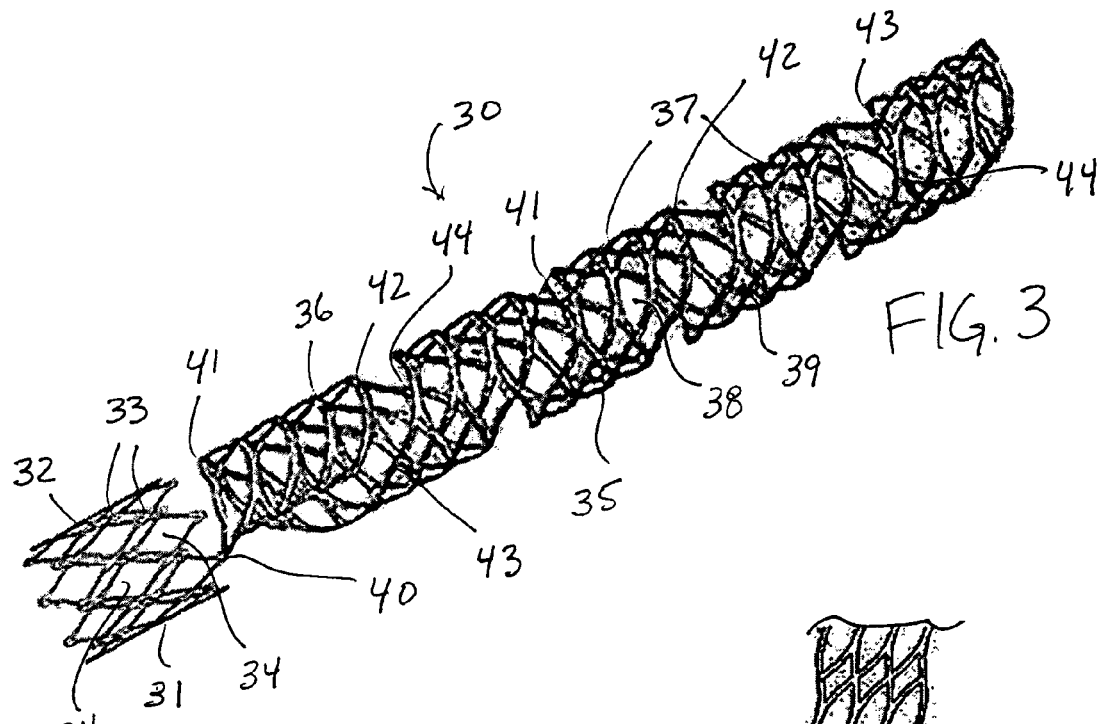
FIG. 3 is a side view of an alternative embodiment of a vascular prosthesis of the present invention.
Figure 4:
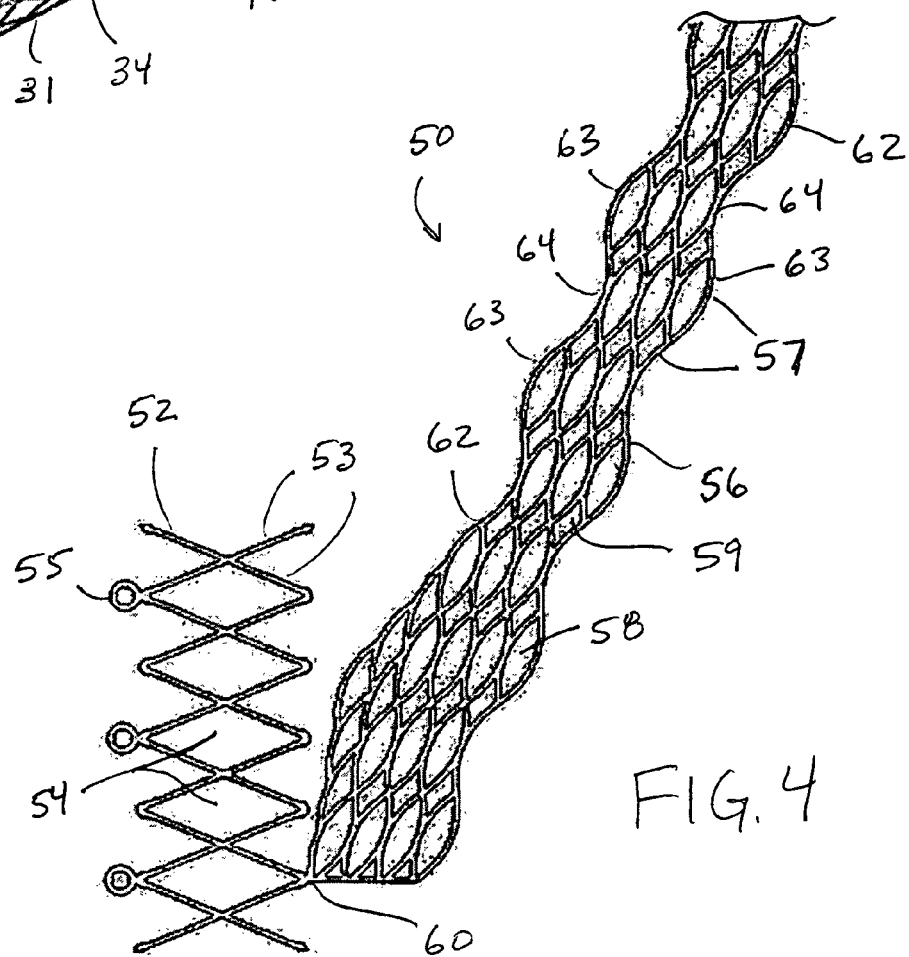
FIG. 4 is a plan view of another alternative embodiment of a vascular prosthesis of the present invention in an unrolled position.

Referring now to FIGS. 3 and 4, further alternative embodiments of vascular prostheses of the present invention are described. Vascular prostheses 30 and 50 are constructed as described in commonly assigned U.S. Patent Publication No. 2004/0122504 and each includes a radially expanding distal section coupled to proximal helical section. The distal section of the prosthesis is deployed from a delivery catheter first to fix the distal extremity of the prosthesis at a desired known location within a target vessel, thereby providing greater accuracy in deploying the proximal helical body section of the prosthesis. Prostheses 30 and 50 may be delivered within a patient's vessel using the apparatus described in commonly assigned U.S. Patent Publication No. 2004/0158308, which is incorporated herein by reference.

More specifically, with respect to prosthesis 30 of FIG. 3, distal section 31 comprises ring-shaped structure 32 having a plurality of struts 33 defining a double row of diamond-shaped openings 34. Ring structure 32 preferably is laser cut from a solid tube to form the desired pattern of struts. Proximal helical section 35 preferably comprises a helical mesh formed of cells 36 that define a plurality of substantially flat turns 37. Cells 36 may include a multiplicity of openings provided in different shapes and sizes, as illustrated by larger ellipsoidal openings 38, and smaller diamond-shaped openings 39. Helical section 35 is coupled to distal section 31 at junction 40, which permits helical section 35 articulate to conform to the anatomy of a patient's vessel.

In accordance with the principles of the present invention, proximal helical section 35 also includes distal edge 41 and proximal edge 42. The alternating ellipsoidal and diamond-shaped openings of cells 36 are aligned along a helical axis of the prosthesis, and produce a series of crests 43 and troughs 44 along each of distal edge 41 and proximal edge 42. As depicted in FIG. 3, the crests and troughs of the distal and proximal edges interdigitate when the stent assumes its deployed configuration.

Prosthesis 50 of FIG. 4 is constructed similarly to prosthesis 30, except that in distal section 51, ring-shaped structure 52 comprises struts 53 that define a single row of diamond-shaped openings 54. Eyelets 55 are provided at the distal ends of struts 53 to accept radio-opaque marker material. As for the preceding embodiment, ring structure 52 preferably is laser cut from a solid tube to form both distal portion 51 and proximal helical section 56. Proximal helical section 56 preferably comprises a helical mesh formed of cells 57 that define a plurality of substantially flat turns. Cells 57 have a multiplicity of larger ellipsoidal openings 58 and smaller diamond-shaped openings 59. Helical section 56 is coupled to distal section 51 at junction 60, which permits helical section 56 articulate to conform to the anatomy of a patient's vessel.

As for the preceding embodiments, proximal helical section 56 also includes distal edge 61 and proximal edge 62. The alternating ellipsoidal and diamond-shaped openings of cells 57 are aligned along a helical axis of the prosthesis, and produce a series of crests 63 and troughs 64 along each of distal edge 61 and proximal edge 62. The crests and troughs of the distal and proximal edges interdigitate when the stent assumes its deployed configuration.

In accordance with yet another aspect of the present invention, the vascular prostheses of the present invention may be coated or otherwise impregnated with therapeutic agents to deliver the agent to a desired location within a target vessel, for example, to treat an aneurysm or prevent restenosis. The prosthesis may have the therapeutic agent deposited in internal or external dimples or through-holes in the struts, an elastomeric polymer and/or applied to solid regions of one or more turns of the prosthesis.

Suitable therapeutic agents may include, for example, anti-platelet drugs, anticoagulant drugs, agents used for purposes of providing gene therapy to a target region, or any other agent, and may be tailored for a particular application. Radio-paque markers also may be selectively disposed on turns of the helical body of the prosthesis in the vicinity of the therapeutic agents to facilitate alignment of the therapeutic agents with a target site of a vessel wall. Advantageously, higher doses of such agents may be provided using the vascular prosthesis of the present invention, compared to previously known stents having interconnected struts, due to the increased surface area associated with the helical body and the relative independence of the radial strength to strut area.

As a further alternative, one or more turns of the prosthesis may be selectively coated with elastomeric polymer, such as polyurethane, for example, to partially or fully cover selected regions of the prosthesis. For example, an elastomeric polymer may be disposed on one arc of the circumference of proximal helical section to overlay an aneurysm and reduce blood flow into a sac of the aneurysm. Additionally, a therapeutic agent may be disposed on or impregnated into the elastomeric polymer, which increases the working surface area of the proximal helical section.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. A vascular prosthesis for implantation in a body vessel, the vascular prosthesis comprising:
    a helical section configured to transition between a contracted, wound-down delivery configuration and an unconstrained, unwound deployed configuration, the helical section comprising at least one unconnected turn extending substantially more than 360° along a helical path when in the deployed configuration, each said turn having a distal edge and a proximal edge;
    the helical section comprising a flat ribbon of material having a multiplicity of openings formed therethrough, at least some of the multiplicity of openings define ellipsoidal openings;
    the distal and proximal edges each defining a series of generally convex crests and generally concave troughs configured so that in the deployed configuration a series of adjacent crests along the distal edge interdigitates with a series of adjacent troughs along an adjacent proximal edge;
    said series of adjacent interdigitating crests along said distal edge extending at least half way into said series of adjacent troughs along said proximal edge; and
    said series of adjacent interdigitating crests and troughs extending along at least half of the helical section;
    whereby the interdigitating crests and troughs improve the coverage and support of the body vessel.

2. The vascular prosthesis of claim 1 wherein, in the deployed configuration, the series of crests and troughs along the proximal edge is spaced apart from the series of crests and troughs along the distal edge.

3. The vascular prosthesis of claim 1 wherein the helical section comprises a shape memory material.

4. The vascular prosthesis of claim 1 wherein at least some of the ellipsoidal openings are circular openings.

5. The vascular prosthesis of claim 1 wherein the openings are defined by a feature disposed in alignment along a helical axis of the prosthesis.

6. The vascular prosthesis of claim 1 wherein the series of crests and troughs has a repetitive pattern and defines a wave-like configuration.

7. The vascular prosthesis of claim 1 wherein the series of crests and troughs has a repetitive pattern and defines a zig-zag configuration.

8. The vascular prosthesis of claim 1 further comprising a therapeutic agent disposed on the helical section.

9. The vascular prosthesis of claim 1 wherein said series of adjacent interdigitating crests and troughs extend along the entire helical section.

* * * * *